US00PP27115P2

(12) United States Plant Patent
Heemskerk

(10) Patent No.: US PP27,115 P2
(45) Date of Patent: Aug. 30, 2016

(54) ***HEMEROCALLIS* PLANT NAMED 'VER00112'**

(50) Latin Name: ***Hemerocallis* hybrid**
Varietal Denomination: VER00112

(71) Applicant: Gerardus J. C. M. Heemskerk, Noordwijk (NL)

(72) Inventor: Gerardus J. C. M. Heemskerk, Noordwijk (NL)

( * ) Notice: Subject to any disclaimer, the term of this patent is extended or adjusted under 35 U.S.C. 154(b) by 86 days.

(21) Appl. No.: 14/544,147

(22) Filed: Dec. 2, 2014

(51) Int. Cl.
*A01H 5/02* (2006.01)

(52) U.S. Cl.
USPC ..... Plt./312

(58) Field of Classification Search
USPC ..... Plt./312
See application file for complete search history.

*Primary Examiner* — Annette Para
(74) *Attorney, Agent, or Firm* — Penny J. Aguirre

(57) ABSTRACT

A new cultivar of *Hemerocallis* named 'VER00112' that is characterized by its flowers that are creamy yellow in color with a green throat, its everblooming habit; blooming from June to October in The Netherlands, and its compact and dormant plant habit.

2 Drawing Sheets

Botanical classification: *Hemerocallis* hybrid.
Cultivar designation: 'VER00112'.

BACKGROUND OF THE INVENTION

The present invention relates to a new and distinct cultivar of *Hemerocallis* plant of hybrid origin, botanically known as *Hemerocallis* 'VER00112' and will be referred to hereafter by its cultivar name, 'VER00112'.

The new cultivar was developed through on on-going breeding program conducted by the Inventor in Noordwijk, The Netherlands. The objectives of the breeding program are to develop new cultivars of *Hemerocallis* that are everblooming with compact plant habits in a range of flower colors.

The new cultivar arose from crosses made in summer of 2006. Proprietary seed parent lines were pollinated with a mixture of pollen collected from proprietary pollen parents and the collected seeds were pooled and sown for evaluation. 'VER00112' was selected as a single unique plant from the resulting seedlings in summer of 2009. The specific parents are unknown and none of the possible parent plants are named or patented.

Asexual propagation of the new cultivar was first accomplished by division in Noordwijk, The Netherlands in 2009 by the Inventor. Asexual propagation by division and tissue culture has determined that the characteristics of this cultivar are stable and are reproduced true to type in successive generations.

SUMMARY OF THE INVENTION

The following traits have been repeatedly observed and represent the characteristics of 'VER00112'. These attributes in combination distinguish 'VER00112' as a new and distinct cultivar of *Hemerocallis*.

1. 'VER00112' exhibits flowers that are creamy yellow in color with a green throat.
2. 'VER00112' exhibits an everblooming habit; blooming from June to October in The Netherlands.

3. 'VER00112' exhibits a compact and dormant plant habit.

The new cultivar can be most closely compared to the cultivars 'Longfields Pearl' (not patented) and 'Ice Carnival' (not patented). Both cultivars are similar to 'VER00112' in flower coloration. 'Longfields Pearl' differs from 'VER00112' in having flower petals margins that are less undulating, in having larger and longer leaves, taller flowering scapes, and in having a reblooming habit rather than everblooming. 'Ice Carnival' differs from 'VER00112' in having larger flowers, much taller flowering scapes, and in lacking an everblooming habit.

BRIEF DESCRIPTION OF THE DRAWINGS

The accompanying colored photographs illustrate the overall appearance and distinct characteristics of the new *Hemerocallis*. The photographs were taken of a 6 month-old plant of 'VER00112' as field grown in Noordwijk, The Netherlands and placed in a container for the photographs.

The photograph in FIG. 1 provides a side view of 'VER00112' in bloom and depicts its compact plant habit.

Figure 1:
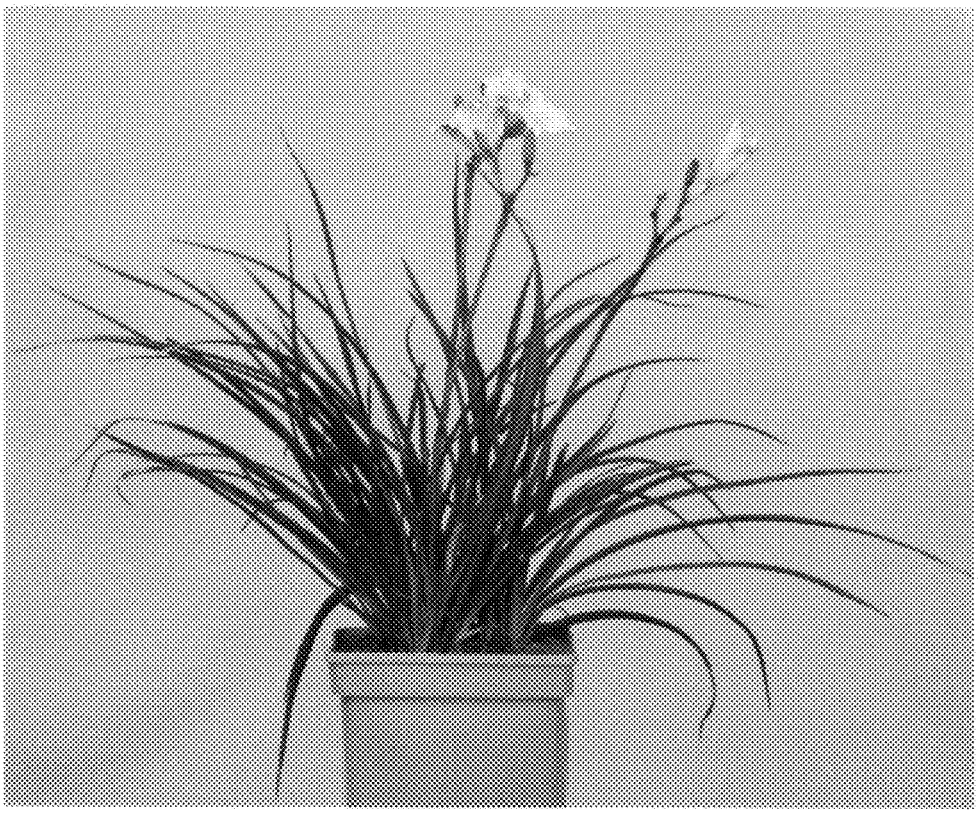
Figure 2:
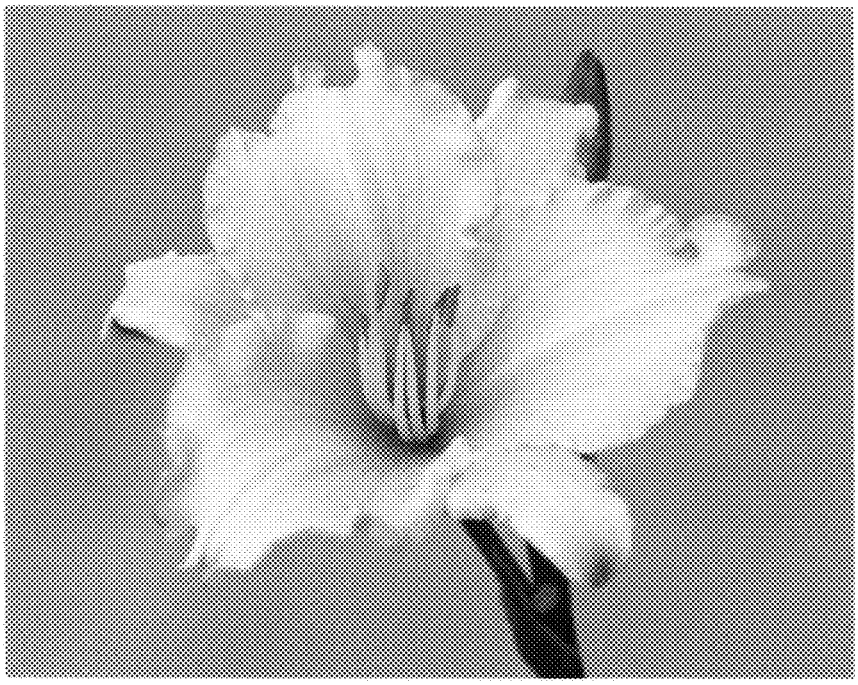

The photograph in FIG. 2 provides a close-up view of a flower of 'VER00112'.

Figure 3:
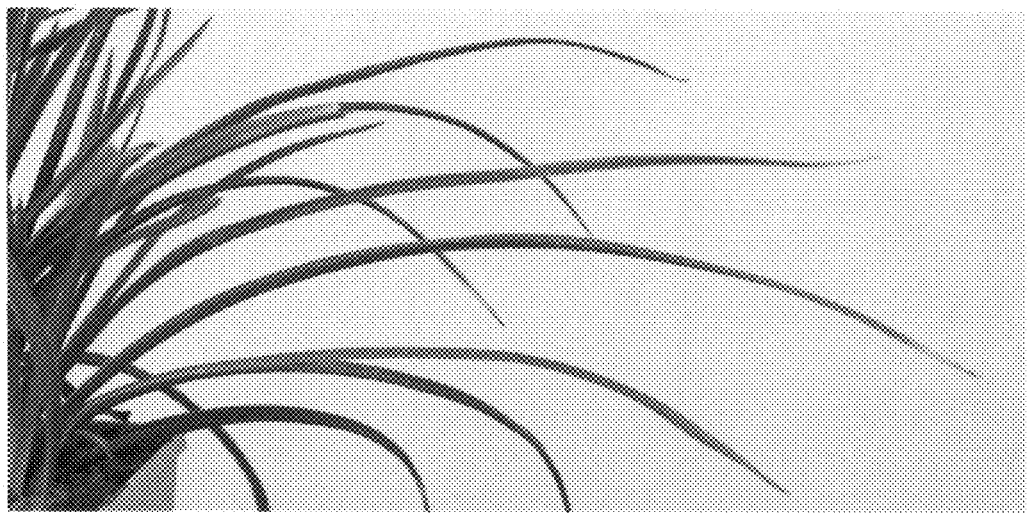

The photograph in FIG. 3 provides a close-up view of the foliage of 'VER00112'.

The colors in the photographs are as close as possible with the digital photography and printing techniques utilized and the color codes in the detailed botanical description accurately describe the new *Hemerocallis*.

DETAILED BOTANICAL DESCRIPTION OF THE PLANT

The following is a detailed description of 6 month-old plants of the new cultivar as field grown outdoors in Noordwijk, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—Everblooming from June to October in The Netherlands.

*Plant type.*—Herbaceous perennial, dormant type.

*Plant habit.*—Compact, grass-like foliage.

*Height and spread.*—Reaches about 40 cm in height to top of foliage and 44 cm in height to top of inflorescence and 40 cm in spread (after two years in the garden).

*Hardiness.*—At least in U.S.D.A. Zone 5.

*Diseases.*—No disease resistance or susceptibility has been observed.

*Root description.*—Fibrous roots.

*Propagation.*—Division and tissue culture.

*Growth rate.*—Vigorous, 4 months to fully root a single fan division in a 11-cm container and 8 months to produce a No. 1 division in the field from a single fan.

Foliage description:

*Leaf shape.*—Linear, strongly carinate, curved.

*Leaf division.*—Simple.

*Leaf base.*—Decurrent.

*Leaf apex.*—Long acute with a short apiculate tip.

*Leaf venation.*—Parrallel, upper and lower surface color 143A.

*Leaf margins.*—Entire.

*Leaf attachment.*—Decurrent, no petioles.

*Leaf arrangement.*—Equitant, fan-shaped.

*Leaf orientation.*—Held upright to slightly pendulant.

*Leaf surface.*—Both surfaces glabrous, upper surface moderately glossy, lower surface matte.

*Leaf color.*—Young leaves (upper and lower surface); 143A, mature leaves upper surface; color between 137B and 143A, mature leaves lower surface; color between 143A and 146A.

*Leaf size.*—Up to 43.4 cm in length, an average of 0.8 cm in width.

*Leaf quantity.*—Average of 10 per rosette.

Flower scape description (peduncle):

*Scape shape.*—Oval to flattened oval, pithy.

*Scape number.*—1 per fan at one time, continuously produced during bloom season.

*Scape aspect.*—Straight, held at an average angle of 85° to soil level.

*Scape size.*—Average of 36.3 cm in length and 5 mm in width.

*Scape color.*—Color between 143B and 144A.

*Scape surface.*—Glabrous, slight sheen.

*Scape branching.*—None.

Flower description:

*Inflorescence type.*—Scape bearing a panicle of single flowers, 1 to 2 flowers open at a time.

*Inflorescence size.*—Varies with opening of flowers, an average of 9.7 cm in width and 10.5 cm in depth.

*Lastingness of flowers.*—About 24 hours, self cleaning.

*Flower size.*—An average of 7.6 cm in length and 7.9 cm in diameter.

*Flower fragrance.*—Faint, slightly acidic and pleasant.

*Flower number.*—Average of 8 flowers and bud per scape, average of 48 per plant.

*Flower aspect.*—Upright to outward.

*Flower bud.*—Narrow obovate to oblong in shape, average of 4.5 cm in length and 1 cm in width, color 151B to 151C with base N144D and apex 144A.

*Rate of flower opening.*—About 20% of flowers open at a time, about 4 weeks for all flowers to open per scape.

*Flower attachment.*—Petiolate.

*Petals.*—3, obovate in shape, average of 8 cm in length and 3.6 cm in width, margins undulate, and moderately ruffled, apex retuse and curled backwards, base fused (lower 22%), slightly recurved in aspect, color upper surface opening and fully open; color between 14D and 15D, 15A near margins, center stripe (main vein) 11C, base N144B (throat), inner tube 150C, color lower surface opening and mature; color between 15D and 16D, 15A near margins, base and tube 150B, both surfaces slightly velvety.

*Sepals.*—3, rotate in arrangement, average of 7.8 cm in length, 1.8 cm in width, narrowly elliptic in shape, entire margins, base cuneate with lower portion fused (22%), acute apex, color upper surface opening and mature; 10A to 10B, base N144B, tube 150C, color lower surface opening and mature; 12A to 12B, margins 10C to 10D, center tinged with 144C, apex 144A, base and tube 150B, both surfaces glabrous, matte and slightly velvety.

*Pedicels.*—Up to 3 cm in length and 3 mm in width, oval in shape, strong and stout, color a blend of 143A, glabrous surface.

*Pedicel leaf.*—Average of 1 per pedicel, lanceolate in shape, 144A in color on both surfaces, average of 2 cm in length and 1.5 cm in width, sheathed base, narrowly acuminate apex, glabrous on both surfaces.

Reproductive organs:

*Gynoecium.*—Pistil; 1, about 7.3 cm in length, style; 7.2 cm in length, 11C in color with base 1C, stigmas; crested, 11C in color, ovary; oblong in shape, 143B in color.

*Androecium.*—Stamens; 6, anthers; narrowly oblong in shape, 5 mm in length and N200A in color; filament; 3.6 cm in length, 11B to 11C in color, pollen; moderate to high in quantity and 17A in color.

*Fruit/seeds.*—None observed.

It is claimed:

1. A new and distinct cultivar of *Hemerocallis* plant named 'VER00112' as herein illustrated and described.

* * * * *